United States Patent
Norell

[11] Patent Number: 5,873,820
[45] Date of Patent: Feb. 23, 1999

[54] VAGINAL SPECULUM

[76] Inventor: Nils-Erik Norell, Blomstervägen 7, Bollnäs, Sweden, 5-821 40

[21] Appl. No.: 981,668
[22] PCT Filed: May 22, 1996
[86] PCT No.: PCT/SE96/00663
  § 371 Date: Dec. 31, 1997
  § 102(e) Date: Dec. 31, 1997
[87] PCT Pub. No.: WO97/01983
  PCT Pub. Date: Jan. 23, 1997

[30] Foreign Application Priority Data

Jul. 4, 1995 [SE] Sweden .................. 9502425-3

[51] Int. Cl.[6] .................. A61B 1/32; A61B 1/303
[52] U.S. Cl. .................. 600/220; 600/223
[58] Field of Search .................. 600/220, 221, 600/222, 223

[56] References Cited

U.S. PATENT DOCUMENTS

| | | | |
|---|---|---|---|
| 2,954,025 | 9/1960 | Grieshaber | 600/220 |
| 3,716,047 | 2/1973 | Moore et al. | 600/222 |
| 3,789,835 | 2/1974 | Whitman | 600/223 |
| 3,817,242 | 6/1974 | Uddenberg . | |
| 3,847,143 | 11/1974 | Cotex et al. | 600/220 |
| 4,807,600 | 2/1989 | Hayes . | |
| 4,971,036 | 11/1990 | Collins | 600/220 |
| 5,072,720 | 12/1991 | Francis et al. | 600/220 |
| 5,499,964 | 3/1996 | Beck et al. | 600/220 |

FOREIGN PATENT DOCUMENTS 466379 2/1992 Sweden .

Primary Examiner—Paul J. Hirsch

[57] ABSTRACT

A vaginal speculum comprises two elements (1, 2) having on one hand a spoon part possible to insert in a woman's vagina (3, 5) and on the other hand an oblique handle part (4, 6). After insertion in the vagina, the spoon parts are movable through displacement of the handle parts so that said parts may widen the vagina. There is an aperture of inspection in one handle part (4), the handle parts (4, 6) having co-operating looking means for locking the parts (1, 2) in relation to each other. The upper as well as the lower spoon part (3, 5) have longitudinally curved shape. More precisely, said spoon parts have such a shape that they diverge with at least 30° from concavely curved intermediate portions (17, 17') towards convexly curved portions (18, 18'), the distance between the convexly curved portions (18, 18') being considerably larger than the corresponding distance between the concavely curved portions (17, 17'). In such a way, the pinching muscle of the opening of the vagina reliably retains the spoon parts inside the vagina.

7 Claims, 5 Drawing Sheets

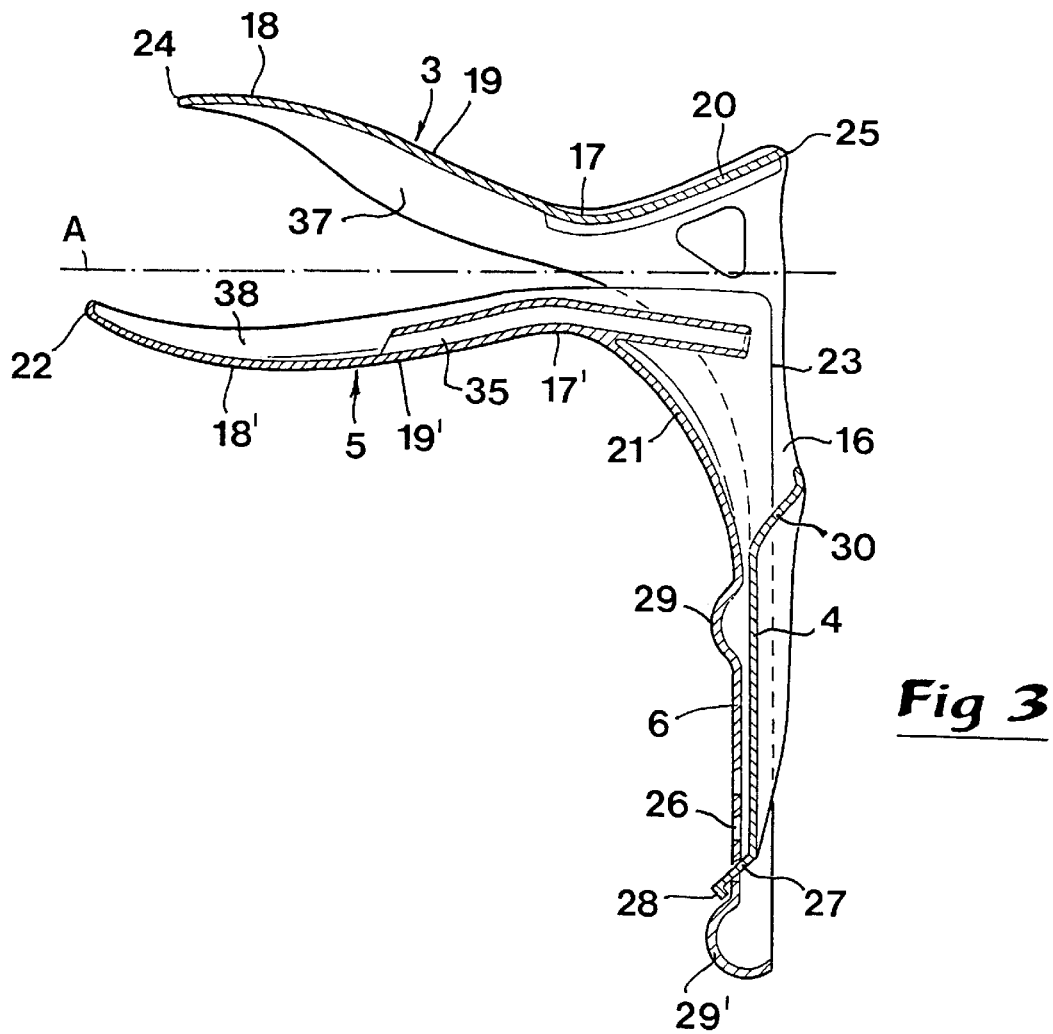
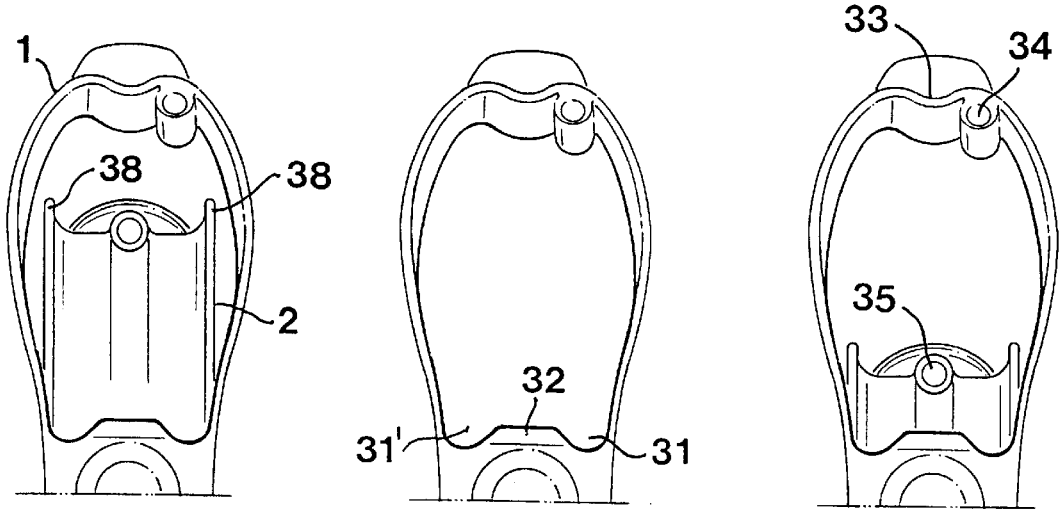

ively can be continued. At worst, the work has to be
completely interrupted after an ejection. Another disadvantage is that the upper spoon part, or duckbill part, as well as the lower one are, in the main, equally wide the whole way backwards from the front end or tip of the spoon part. This equally wide shape may in practice cause pains or inconvenience for the woman in connection with the squeezing in of the spoons parts through the opening of the vagina and the vagina, in that the tissues are initially hit by front portions of the spoon parts which are, in the main, as wide as the rear ones. One further disadvantage of the known speculum device is that the upper spoon part, by the geometrical design thereof, exerts a considerable pressure on the urethra which is squeezed in between the upper spoon part and the hard pubic bone when the spoon parts are maximally distanced from each other for the purpose of maximally widening the vagina. Further, a disadvantage is that the interior of the vagina can not be widened much more than what the maximum widening of the pinching muscle or the opening of the vagina admits.

VAGINAL SPECULUM

TECHNICAL FIELD OF THE INVENTION

This invention relates to a vaginal speculum comprising two mutually separable, upper and lower elements, each of which has a spoon part which is insertable in the woman's vagina, said spoon part being integral with a handle part directed at an angle thereto, and which elements from an initial position, in which said spoon parts are approached to each other, are to displaceably movable in relation to each other so as to widen the vagina after insertion of the spoon parts therein and thereby enable inspection and/or insertion of instruments in the interior of the vagina, more precisely through an aperture in the handle part of the upper speculum element, said handle parts having co-operating locking means by means of which the elements may be locked in the desired adjustment positions in relation to each other, and the upper as well as the lower spoon part having a longitudinally curved shape, more precisely such a shape that said spoon parts diverge from concavely curved intermediate portions towards convexly curved portions.

Vaginal speculum of the above-mentioned kind are used on one hand in connection with gynecological examinations in which the interior of the vagina, e.g. the mouth of the womb. is ocularly inspected, and on the other hand also in connection with more or less complicated operations of the interior of the vagina, e.g. in order to remedy cancer diseases or to take vaginal smear tests. Such operations may be performed with conventional surgical knives as well as by the use of modern laser operational technology, and also with diathermy.

A similar vaginal speculum is also known in SE 9002345-8. In this case, however, the two spoon parts are, in the main, completely straight and parallel to each other, and therefore the risk of ejection is even more explicit than in the speculum according to DK 125 056.

OBJECTS AND FEATURES OF THE INVENTION

The present invention aims at obviating the above-mentioned disadvantages and shortcomings of the specula disclosed in DK 125 056 and SE 9002345-8 and at creating an improved speculum. Thus, a primary object of the invention is to provide a speculum which is automatically retained in the vagina in a reliable way as soon as the spoon parts are maximally distanced from each other and locked in the desired adjustment position. Furthermore, a reliable retention should be guaranteed even if the speculum is drawn out a bit from the very inner position thereof in the vagina. Another object of the invention is to create a speculum which may be smoothly inserted in the vagina in such a way that the woman's pains and inconvenience are reduced to a minimum. A further object of the invention is to create a speculum which does not exert a considerable pressure on the urethra during usage. An object is also to create a speculum which admits larger widening of the interior of the vagina than previously. Other objects of the invention are to create a speculum which is easy to use, in particular considering the possibilities to displace and lock the spoon parts in relation to each other, and which is easy and cheap to manufacture.

PRIOR ART

A vaginal speculum of the kind initially related to is disclosed in DK 125 056. In this known speculum, the spoon parts are, in the main, equally long and only slightly curved. Apart from the fact that the two spoon parts have cross-section-wise vaulted or rounded shape, the lower spoon part is thus substantially straight, while the upper one has an oblique wall portion between the concave and the convex portions, said portions converging in their distal, free end portions in the direction towards each other. The angle between the straight lower spoon part and the oblique wall portion of the upper spoon part is less than lot 10°. For reasons which are clear from below, this geometrical shape is disadvantageous.

The interior of the woman's vagina extending between the opening of the vagina and the mouth of the womb or the portio is surrounded by muscles which certainly are weaker than the powerful pinching muscle in connection with the opening of the vagina, but which nonetheless may exert considerable contraction force. These vaginal muscles may be activated already by the fact that the woman is tense, faced with an examination or operation being close at hand. At times said muscles may also be activated and contract the vagina as a consequence of such trivial a circumstance as an attack of coughing. When the vaginal muscles for one reason or another, without the woman's conscious control, are activated and contract the vagina, the above-mentioned geometrical shape of the speculum disclosed in DK 125 056 entails that said speculum unintentionally is ejected from the vagina. In practice, this is something which to a great extent obstructs the physician's work. Thus, in most situations, the physician's two hands are engaged by handling various instruments and that is why it is inconceivable to use one of the hands only to hold the speculum device in place. If an unintentional ejection occurs in this connection, the instruments must be removed and the speculum device be put back in place before the operation and the examination respec- According to the invention, at least the primary object is attained by the features defined in the characterizing clause of claim 1. Preferred embodiments of the invention are furthermore defined in the dependent claims.

FURTHER ELUCIDATION OF THE PRIOR ART

In DE 514 195 and U.S. Pat. No. 4,807,600 vaginal specula are disclosed the spoon parts of which have a slightly vaulted or rounded basic shape. However, in these two cases, the spoon parts are pivotable in relation to each other by the fact that the upper spoon part is articulately connected to the appurtenant handle part and adjustable in different positions by means of a mechanical lock device.

However, such lock devices are inappropriate in connections with gynecological work inasmuch as the woman's very delicate tissues in the area of the vagina may get jammed in connection with manipulation of the lock device. Unlike these specula, the present invention is based on the use of angular speculum elements each of which having the spoon part thereof integral with the appurtenant handle part.

It may also be mentioned that a vaginal speculum with a hinged upper spoon part is disclosed in U.S. Pat. No. 3,815,565. However, in this case, the spoon parts are, in the main, completely straight.

BRIEF DESCRIPTION OF THE APPENDED DRAWINGS

In the drawings;

FIG. 1 is a perspective view of a speculum device according to the invention,

FIG. 2 is a schematic picture illustrating the woman's anatomy in connection with the vagina, the speculum according to FIG. 1 being shown inserted in the vagina, FIG. 3 is a longitudinal section through the two elements of which the speculum is composed, FIG. 4 is a partial end view showing an aperture of inspection in the handle part of the upper speculum element, the two spoon parts of the speculum elements being maximally approached to each other, FIG. 5 is a corresponding end view showing the aperture of inspection when the spoon parts of the speculum elements are far distanced from each other, FIG. 6 is an analogous end view showing the aperture of inspection when the spoon parts are adjusted in an intermediate position, FIG. 7 is an exploded view showing the two elements of the speculum spaced-apart, FIG. 8 is a side view illustrating the displaceability between the two elements of the speculum, FIG. 9–11 are side views showing the two elements of the speculum in different positions during insertion in a vagina, and FIG. 12–14 are planar views from above corresponding to the side views according to FIGS. 9 to 11.

DETAILED DESCRIPTION OF A PREFERRED EMBODIMENT OR THE INVENTION

Figure 1:
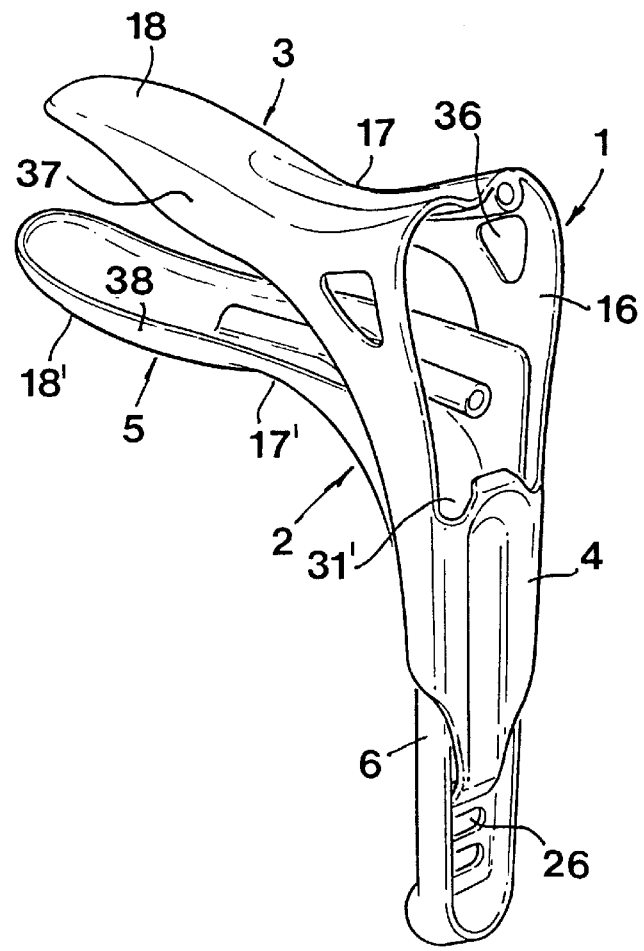
Figure 7:
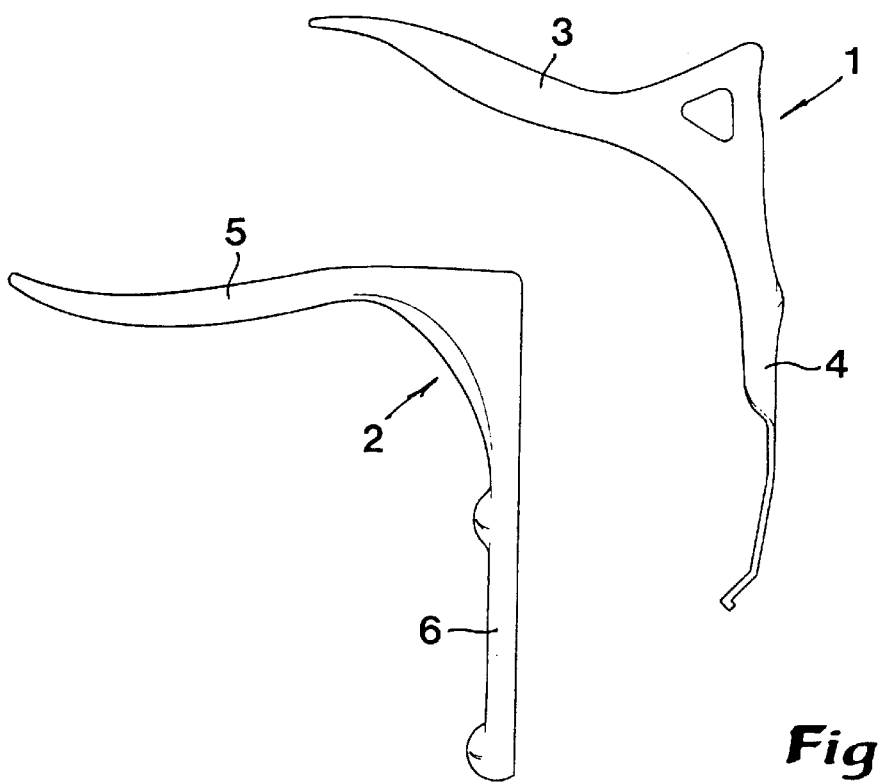

The speculum shown in FIG. 1 comprises two mutually displaceably movable and separable elements, generally designated 1 and 2 respectively. The element 1 comprises a first or upper spoon part 3 and a handle part 4 directed at an angle thereto. In an analogous way, the element 2 comprises a spoon part 5 and a handle part 6. As may be clearly seen in FIG. 7, the two speculum elements are, in the main, L-shaped, each spoon part being integral with the appurtenant handle part. In practice, the two elements may advantageously be made of molded, stiff plastic.

Figure 2:
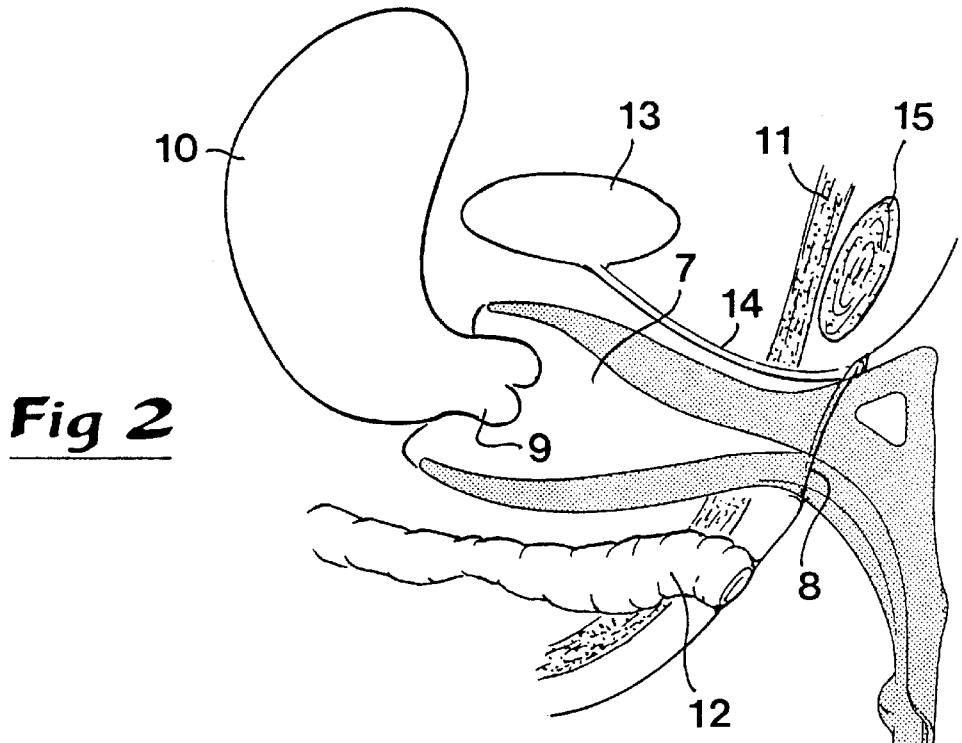

Before the invention is described in more detail, reference is made to FIG. 2 schematically illustrating the anatomy in connection with a woman's vagina. The vagina 7 itself consists of a hollow surrounded by muscles extending from the outer opening of the vagina to the mouth or the portio 9 of a womb 10. The main part of the vagina 7 is located inside of the pelvic floor muscle 11 and above the colon 12. Above the vagina there is the urinary bladder 13 and the urethra 14. Above the opening of the vagina 8, surrounded by a strong pinching muscle, there is the firm and hard pubic bone 15.

Although the anatomy of the womb and the portio may vary to a great extent, it can generally be noted that the portio of the womb is located in the area of the inner end of the vagina 7.

Reference is now made to FIGS. 1 and 3 simultaneously, in which it may be seen how a wide aperture 16 is recessed in the upper part of the handle part 4 of the element 1. This aperture is henceforth denominated an aperture of inspection, although the same also serves the purpose of inserting various instruments in the vagina. As may be most clearly seen in FIG. 3, the upper spoon part 3 as well as the lower spoon part 5 have a longitudinally curved shape. More precisely, the spoon parts have such a shape that said spoon parts diverge from the concavely curved intermediate portions 17, 17' in the direction towards the convexly curved portions 18, 18' near the free ends of the spoon parts. In relation to the imaginary axial line A extending, in the main, perpendicularly to the handle parts 4, 6, oblique, slightly arched wall portions 19, 19' thus extend between the concavely curved wall portions 17, 17' and the convexly. curved wall portions 18, 18'. In the example, the oblique angle between the wall portion 19 and the axial line A is about 23°, while the oblique angle between the wall portion 19' and the axial line A amounts to about 13°. In other words, the total angle between the wall portions 19, 19' amounts to about 36°. Tests made have shown that this total angle between the oblique wall portions of the spoon parts should amount to at least 30°. In the preferred embodiments, this angle should be within the range of 33°–45°, preferably within the range of 35°–40°. The relatively large angle in which the wall portions 19, 19' jointly diverge becomes, in this way, large enough to locate the convexly curved wall portions is, 18, 18' at a mutual distance (across the line A) being considerably larger than the corresponding distance between the concavely curved wall portions 17, 17'. In the example, the largest cross-distance between the portions 18, 18' is more than twice as large as the smallest cross-distance between the portions 17, 17'. The concavely curved intermediate portion 17 of the upper spoon part transforms at the back into a wall portion 20 diverging backwards in relation to the axial line A. In a similar way, the concavely curved intermediate portion 17' of the lower spoon part 5 transforms into the handle part 6 via a transition portion 21 being concavely curved in an angle sharply diverging in relation to the line A.

As may be clearly seen in FIG. 3, the lower spoon part is longer than the upper one. In a prototype designed in practice, the lower spoon part has a length of 145 mm (counted from the tip 22 to the back edge 23 of the handle part), while the corresponding length of the upper spoon part is 130 mm (counted from the tip 24 to the back edge 25 of the handle part). The length difference between the two spoon parts should in practice be within the range 10–20 mm.

In the lower part of the handle part 6, a number of elongate apertures 26 are recessed. The lower end of the handle part 4 has an oblique wall portion 27 which at the free end thereof has a hook-like projection 28. The apertures 26 and the hooks 28 constitute a locking means, by means of which the two speculumn elements 1,2 may be kept locked in relation to each other in a desired adjustment position. More precisely, these locking means co-operate in such a way that the hook 28 interlocks towards the lower edge defining the individual aperture 26 through which the oblique wall portion 27 is brought.

The handle part 6 has two rounded bulges 29, 29' forming shoulders for the hand's fingers (index finger and little finger) so as to facilitate the hand's grip of the handle part 6. An analogous shoulder for the same hand's thumb has the shape of an oblique and rounded wall portion 30 on the handle part 4. This wall portion 30 is located immediately below the aperture of inspection 16.

As may be clearly seen in FIGS. 4 to 6, the aperture of inspection 16 transforms at the bottom into two countersinks 31, 31' on both sides of a central wall portion 32. Separately, these countersinks 31, 31' may receive an instrument or tool, e.g. a homeostatic forceps, inserted in the vagina, the laterally adjusted position of the countersink guaranteeing that the tool is held aside, out of the way for manipulations in the center of the aperture of inspection. As may be further seen in FIGS. 4 to 6 in combination with FIG. 3, the upper spoon part 3 is made with a central flute 33 for location below the woman's urethra extending between the aperture of inspection 16 and the concavely curved intermediate portion 17. A duct 34 for e.g. a fibre optic cable for lighting purposes is provided beside the flute 33. Also in the lower spoon part 5, there is a duct 35 through which a tube may be inserted for the suction of blood and other body liquids which may be accumulated on the lower spoon part.

In the transition between the spoon part 3 and the handle part 4 of the upper speculum element 1 there may be holes 36 recessed for the insertion of instruments and tools from the side instead of through the aperture of inspection 16.

Figure 12:
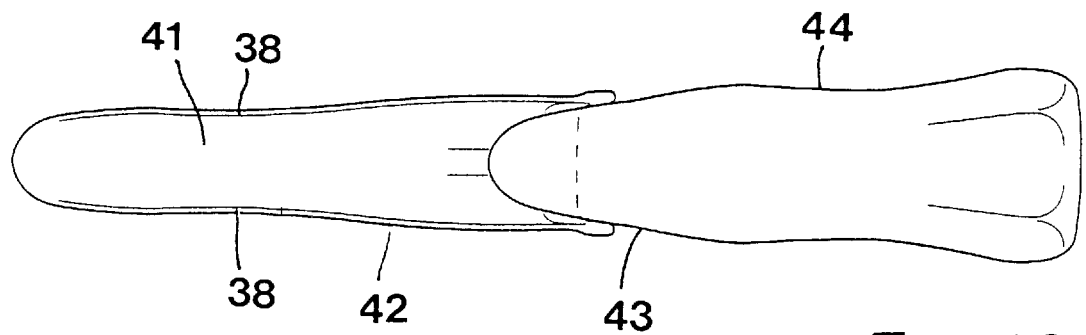
Figure 13:
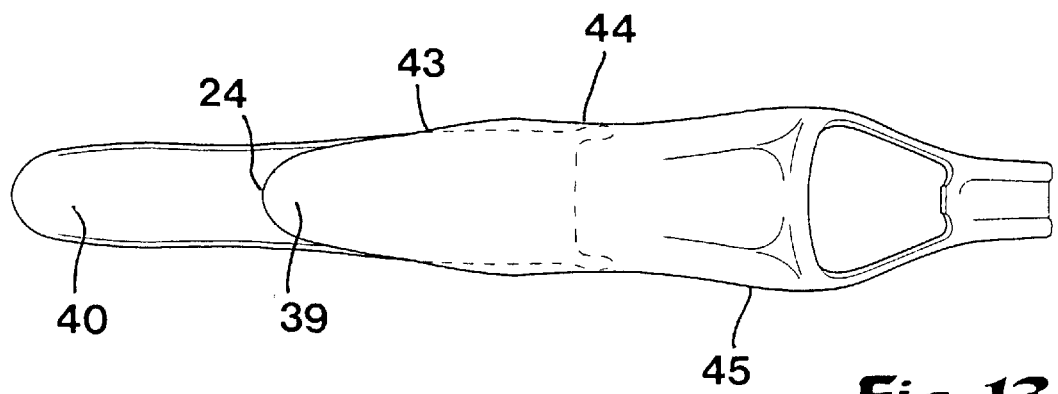
Figure 14:
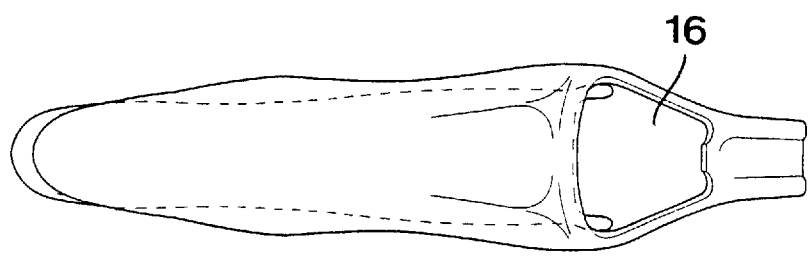

The upper spoon part 3 has side walls 3 extending, in the main, vertically downwards from the opposite long side edges of the central part of the spoon part. In other words, these side walls and the intermediate central part constitute a flute-like configuration. In an analogous way, the upper spoon part 5 includes two side walls 38 extending, in the main, vertically upwards from an intermediate central part. Thus, cross-section-wise, also the lower spoon part is flute-formed. In accordance with a characteristic feature, the upper spoon part is wider in the area of its rear end than the corresponding rear end of the lower spoon part, more precisely inasmuch as the distance between the side walls 37 of the upper part is larger than the distance between corresponding rear portions of the side walls 38 of the lower spoon part. As may be clearly seen in FIG. 3, the height of the side walls 37 is drastcically reduced in connection with the front end or tip of the upper spoon part. As is furthermore evident from FIGS. 12 to 14, the upper spoon part is provided with a tapering front end section 39. More precisely, this tapering front end section is narrower than the front end section designated 40 of the lower spoon part 5. Although the upper spoon part 3, along the main part of the length thereof, is wider than the lower spoon part, the front tip and end section of the upper spoon part may thus be brought down in the flute-like configuration which is defined between the two side walls 38 of the lower spoon part 5. From FIGS. 12 to 14 it is furthermore evident that the upper spoon part as well as the lower one generally taper in the direction of the front end or tip thereof. Thus, in the immediate adjacency to the front section 40 the lower spoon part has a section 41 having mainly parallel side walls, and then the side walls and the intermediate central part are somewhat widened in a rear wedge-shaped section 42. The front end section 39 of the upper spoon pat immediately transforms into a wedge-shapedly diverging section 43 which, in turn, via a section 44 with parallel side walls, in conclusion transforms into another wedge-shapedly diverging section 45. The section 44 as well as the section 45 have a larger width than the rear, wide end section 42 of the lower spoon part.

THE FUNCTION OF THE INVENTION

Figure 8:
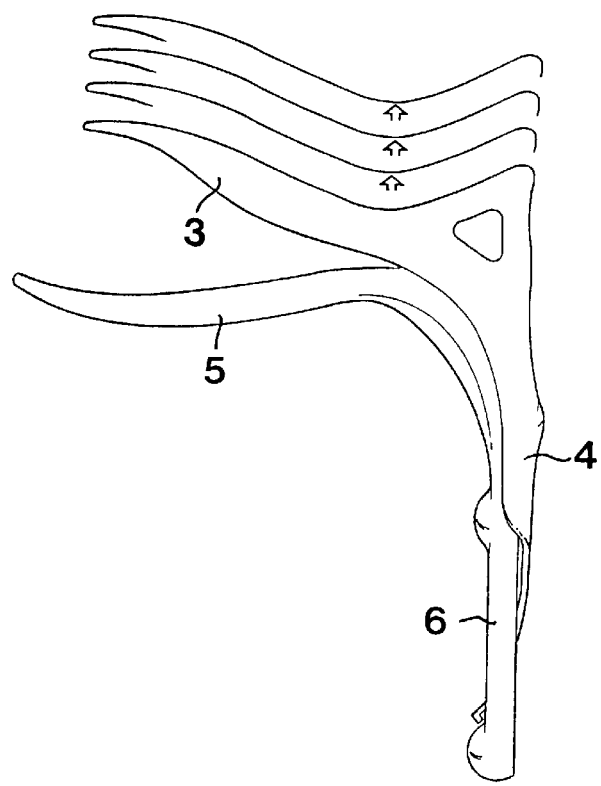
Figure 9:
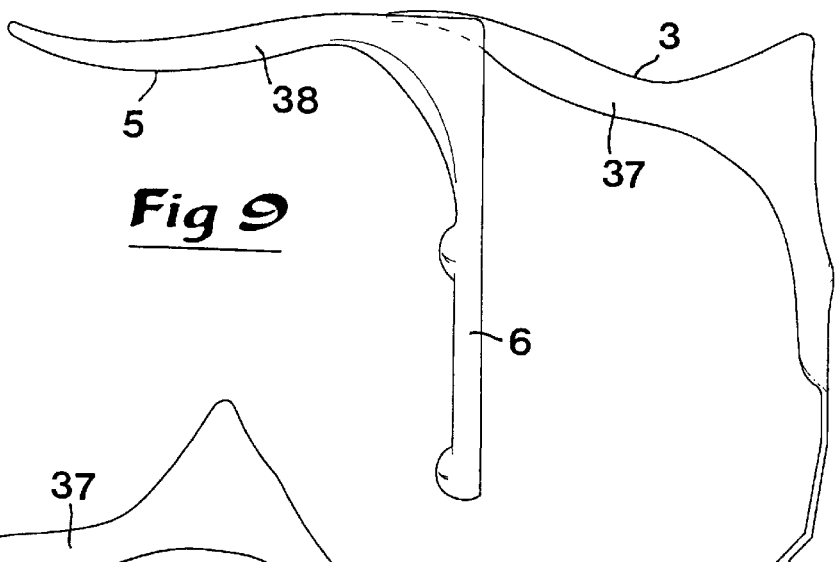
Figure 10:
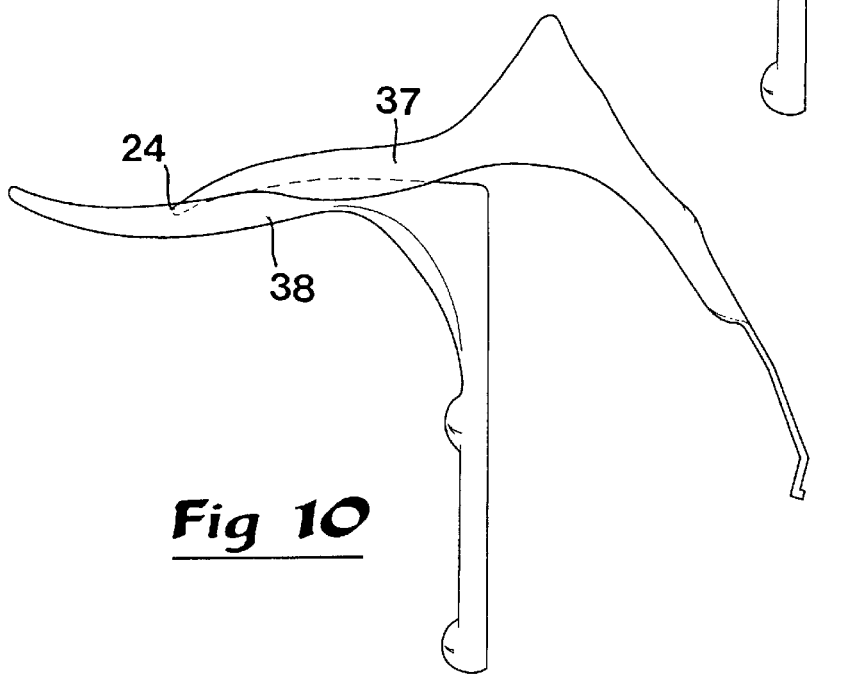
Figure 11:
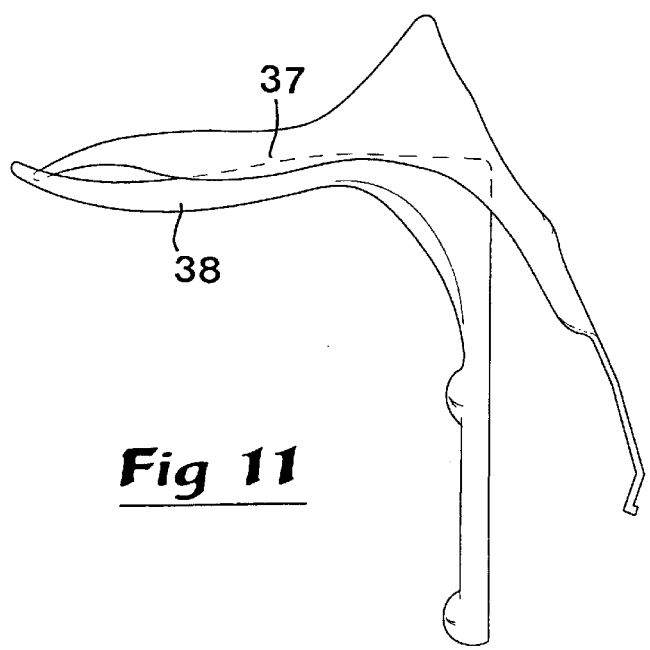

The speculum as described above functions in the following way. The two spoon parts 3, 5 may be inserted in the vagina either simultaneously or separately; however, in both cases the upper spoon part 3 should be pivoted with the tip 24 pointing downwards to the lower spoon part at the passage of the opening of the vagina. When the two spoon parts have been inserted in the vagina via the opening of the vagina, the handle part 4 is pivoted towards the handle part 6 so that the handle parts are located, in the main, mutually in parallel. In this state, the adjustment of the spoon parts 3, 5 is set in dependence on the size of the woman's vagina and the opening of the vagina. This is done by the operator bringing the handle part 4 in the direction upwards with the thumb of the hand (see FIGS. 7 and 8) along the handle part 6 (which is held by the hand's index finger and little finger) until it can be felt that the vagina and the opening of the vagina have been maximally widened. In this position, the hook member 28 is brought into engagement with the nearest aperture 26. By the fact that the muscles of the vagina applies a force to the spoon parts 3, 5 aiming at pivoting the spoon parts in the direction towards each other, forces are applied to the handle parts 4, 6 aiming at pivoting the spoon parts in the direction from each other. However, by the fact that the hook member 28 engages towards the lower edge of the appurtenant aperture, a separation of the handle parts from each other is made impossible. Instead, the handle parts are kept together by a locking force which increases with an increasing force in the muscles of the vagina. Owing to the fact that the spoon parts 3, 5 have the explicit arch-shape characteristic for the invention, said shape implying that the angle between the oblique wall portions 19, 19' is larger than 30° (and as a consequence it follows that the distance between the convexly curved portions 18, 18' is considerably larger than the distance between the concavely curved portions 17, 17'), a reliable retention of the spoon parts inside the vagina is guaranteed as soon as the handle parts are locked in relation to each other. Thus, the woman's pinching muscle in connection with the opening of the vagina is so strong that it is able to hold back the spoon parts widening inward themselves, even if forces are applied thereto by the muscles of the vagina themselves, said forces aiming at ejecting the spoon parts from the vagina. Of course, the retention ability becomes larger, the larger the angle between the spoon portions 19, 19' is and the wider the spoon parts are spaced apart in the area of the convexly curved portions 18, 18'. Estimations have shown that a good retention ability is obtained already when the distance between the portions 18, 18' in the initial position according to FIG. 3 is 50% larger than the distance between the portions 17, 17'. A very good retention ability is obtained when the distance between the portions 18, 18', as shown in FIG. 3, is more than twice as large as the distance between the portions 17, 17'. In all circumstances, the angle between the spoon portions 19, 19' should be at least 30°. By the fact that the lower spoon part 5 is longer than the upper spoon part 3, it is further obtained that the portio 9 is located in a very visible and easily accessible position in the whole anatomic area around the portio. Among elderly women and multipara, the portio is in most cases resting against the bottom of the vagina. By the fact that the lower spoon part is longer than the upper one, it is possible for the physician to "raise up" the portio on the lower spoon part before the upper spoon part meets the portio and obstructs further insertion of the spoon parts in the vagina. Especially among multipara, the portio may be enlarged or prolapsed implying that the spoon parts may be inserted furthest into the vagina only with problems. Nevertheless, by its geometry, the speculum according to the invention may, in an advantageous way, be held in a not fully inserted intermediate position in which said speculum is reliably retained inside of the pinching muscle of the opening of the vagina, thanks to the large angle between the spoon portions 19, 19'. Another advantageous functioning of the speculum device according to the invention is that the urethra 14 may be located in the flute 33 and be housed therein without squeezing pressure being applied thereon between the upper spoon part 3 and the hard pubic bone 15. Furthermore, the tapering shape of the upper spoon part as well as the lower one entails that the insertion of the speculum in the woman's vagina becomes ergonomically lenient in that the tissues successively are pushed aside without being abruptly exposed to extreme pressure forces.

FEASIBLE MODIFICATIONS OF THE INVENTION

The invention is not limited solely to the embodiment described and shown in the drawings. Thus is it is feasible to make the speculum device with other locking means than those shown in the drawings. Further, the spoon parts may be made with considerably wider or higher side walls than those exemplified in the drawings.

I claim:

1. In a vaginal speculum having a pair of mutually separable upper and lower of said elements (1,2), each element having a spoon portion (3,5) integral with a handle portion (4,6) and disposed at an angle thereto, said elements being moveable from an initial position in which the spoon portions (3,5) are in proximity to each other to a position displaceable relative to each other, said handle portion of said upper element having an inspection aperture (16) therein, said handle portions of said upper and lower elements having co-operating locking means (26,28) whereby said elements may be locked in a desired position relative to each other, each said spoon portion (3, 5) of each of said upper and lower elements (1,2) having a longitudinally curved shape diverging from a concavely curved intermediate portion (17, 17') to a convexly curved portion (18,18'), the improvement wherein said intermediate portions have oblique wall portions (19, 19') with an angle between said oblique wall portions of at least 30 degrees and wherein the distance between said convexly curved portions (18,18') of said spoon portions is at least 50% greater than the corresponding distance between said concavely curved portions (17, 17') when said spoon portions are in said initial position in proximity to each other.

2. A vaginal speculum according to claim 1, wherein said upper and lower elements each have a spoon portion with a rear end having side walls (37,38), the spoon portion of said upper element having a greater width at its rear end relative to the width of the corresponding portion of said lower element, the distance between said walls (37) of the spoon portion of the upper element being greater than the distance between said walls of the spoon portion of said lower element, and wherein said upper and lower elements each have a spoon portion with a front end area with the front end area of the spoon portion of the upper element being narrower than the front end area of the spoon portion of said lower element whereby the spoon portion of said upper element may be arranged with its front end between said walls of the spoon portion of the lower element.

3. A vaginal speculum according to claim 1, wherein both said upper and lower spoon portions (3,5) have a taper toward a front end.

4. A vaginal speculum according to claim 2, wherein both said upper and lower spoon portions (3,5) have a taper towards a front end.

5. A vaginal speculum according to claim 1, wherein said inspection aperture has two laterally spaced-apart countersinks (31,31').

6. A vaginal speculum according to claim 2, wherein said inspection aperture has two laterally spaced-apart countersinks (31,31').

7. A vaginal speculum according to claim 3, wherein said inspection aperture has two laterally spaced-apart countersinks (31,31').

* * * * *